United States Patent
Heckel et al.

(10) Patent No.: US 10,634,588 B2
(45) Date of Patent: Apr. 28, 2020

(54) REAGENT FOR THE DISRUPTION OF CELL MATERIAL HAVING A COMPLETELY INTEGRATED INTERNAL STANDARD

(75) Inventors: Dirk Heckel, St. Martin d'Uriage (FR); Katharina Beller, Hilden (DE)

(73) Assignee: QIAGEN GmbH, Hilden (DE)

(*) Notice: Subject to any disclaimer, the term of this patent is extended or adjusted under 35 U.S.C. 154(b) by 0 days.

(21) Appl. No.: 13/825,487

(22) PCT Filed: Sep. 23, 2011

(86) PCT No.: PCT/EP2011/066562
§ 371 (c)(1),
(2), (4) Date: Mar. 21, 2013

(87) PCT Pub. No.: WO2012/038523
PCT Pub. Date: Mar. 29, 2012

(65) Prior Publication Data
US 2013/0236900 A1    Sep. 12, 2013

(30) Foreign Application Priority Data
Sep. 24, 2010  (EP) .................................... 10010447

(51) Int. Cl.
| | |
|---|---|
| C12Q 1/68 | (2018.01) |
| G01N 1/30 | (2006.01) |
| C12Q 1/6806 | (2018.01) |
| C12Q 1/6851 | (2018.01) |
| C12N 1/06 | (2006.01) |

(52) U.S. Cl.
CPC ............... *G01N 1/30* (2013.01); *C12N 1/06* (2013.01); *C12N 1/066* (2013.01); *C12Q 1/6806* (2013.01); *C12Q 1/6851* (2013.01)

(58) Field of Classification Search
None
See application file for complete search history.

(56) References Cited

U.S. PATENT DOCUMENTS 6,617,105 B1* 9/2003 Rudi .................. C12N 15/1013
435/259

OTHER PUBLICATIONS

Kinoshita et al. (J Cell Bio, 1979, vol. 82, p. 688-696).*
Kula et al. (Biotechnology Progress, vol. 3, No. 1, p. 31-42).*
Eissa et al. (Life, 1999, vol. 48, p. 231-236).*
Saraaela et al. (Intl Dairy Journ, 2006, vol. 16, p. 1477-1482).*
Miller et al. (Appl and Environ Microbiol, 1999, 65(11):4715-4724).*
Wu et al. (Enzyme and Microbial Technology, 2005, 37, 102-112) (Year: 2005).*
Liu et al. (Eviron Sci Technol, 2008, 42, 159-165) (Year: 2008).*
International Search Report dated Nov. 29, 2011, for corresponding International Patent Application No. PCT/EP2011/066562 with English Translation, 8 pages.
Dietrich et al., "Fine-tuning of a three-dimensional microcarrier-based angiogenesis assay for the analysis of endothelial-mesenchymal cell co-cultures in fibrin and collagen gels," *Angiogenesis* 9:111-125, 2006.
Doty et al., "Development and validation of an independent positive control for nucleic acid tests for microorganisms that cause septicemia," Abstracts: Sixth International Symposium on Molecular Diagnostics, Medical University of Graz, *Clin Chem Lab Med* 44(4):A8, May 2006, 2 pages.
Kalish et al., "Membrane Isolation on Polylysine-Coated Glass Beads Asymmetry of Bound Membrane," *Biochimica et Biophysica Acta* 506:97-110, 1978.
Klinefelter et al., "Optimizing Testosterone Production by Purified Adult Rat Leydig Cells In Vitro," *In Vitro Cellular & Developmental Biology* 24(6):545-549, 1988.
Sanford et al., "Three-Dimensional Growth of Endothelial Cells in the Microgravity-Based Rotating Wall Vessel Bioreactor," *In Vitro Cell. Dev. Biol.—Animal* 38:493-504, Oct. 2002.
Wöhler et al., "Large scale culturing of normal diploid cells on glass beads using a novel type of culture vessel," *Exptl Cell Res* 74:571-573, 1972.

* cited by examiner

*Primary Examiner* — Stephanie K Mummert
(74) *Attorney, Agent, or Firm* — Seed IP Law Group LLP

(57) ABSTRACT

The present invention relates to a reagent for the disruption of cell material, containing an internal standard that is completely integrated into the reagent for control and evaluation of the completeness of disruption of the cell material and subsequent steps, comprising a step selected from sample preparation, extraction, enrichment, isolation, purification, reverse transcription, amplification and detection of the cell components obtained from the disrupted cells, or a combination of a plurality or all of these steps.

18 Claims, 1 Drawing Sheet
Specification includes a Sequence Listing.

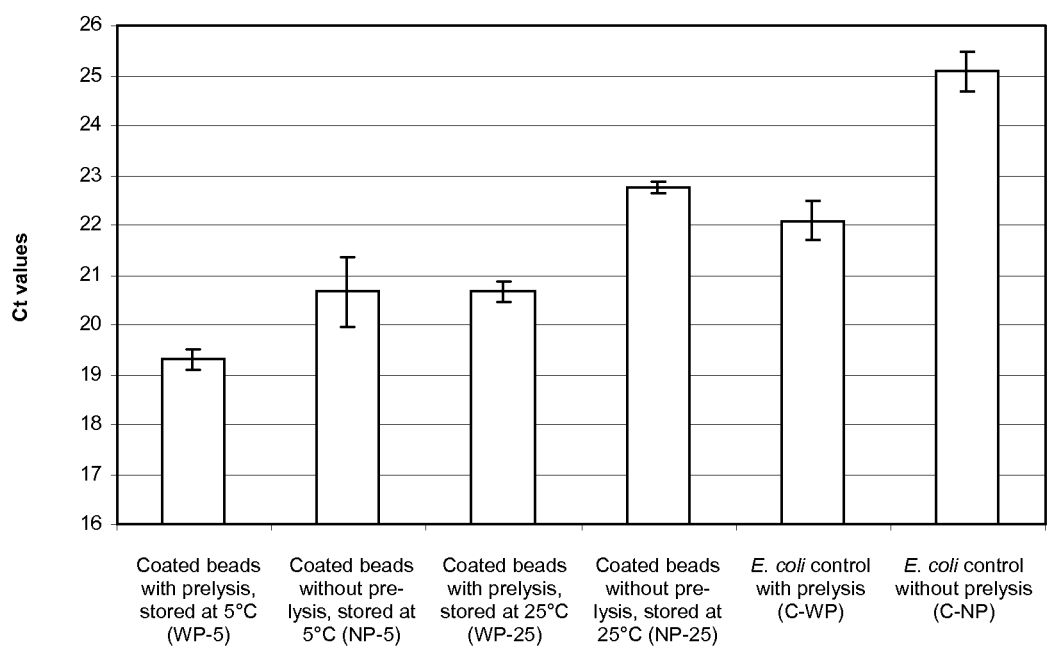

REAGENT FOR THE DISRUPTION OF CELL MATERIAL HAVING A COMPLETELY INTEGRATED INTERNAL STANDARD

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025_447USPC_SEQUENCE_LISTING.txt. The text file is 1 KB, was created on May 23, 2013, and is being submitted electronically via EFS-Web.

The present invention relates to a reagent for disrupting cellular material, containing an internal standard completely integrated into the reagent for the purposes of checking and assessing the completeness of disruption of the cellular material and for the purposes of checking and assessing the efficiency of subsequent steps such as sample preparation, extraction, concentration, isolation, purification, reverse transcription, amplification and detection of the cellular constituents obtained from the disrupted cells or a combination of a plurality of or all of these steps, comprising beads, the surface of which is coated with reference cells as a standard.

The isolation, characterization and analysis of intracellular constituents, especially proteins and nucleic acids (ribonucleic acids (RNA) and deoxyribonucleic acids (DNA)), is of great importance to modern molecular biology. At least since the discovery of the polymerase chain reaction (PCR) in 1983, there has been development of a multiplicity of nucleic acid diagnostic methods, which, for example, are utilized for the detection of diseases and pathogens.

The first step for the isolation and analysis of intracellular constituents is cell disruption (lysis of cells), in order to release the intracellular constituents from the cell. The disruption procedure and the efficiency of disruption have a decisive influence on the total amount of the constituents obtained, their biological activity, integrity and contamination of the material obtained. Over the course of time, a multiplicity of methods for cell lysis has been developed, and of these methods, the important ones are, in particular, enzymatic cell lysis with degradation of cell wall components by enzymes, chemical cell lysis using detergents, bases and chaotropic agents, and mechanical cell lysis, in which the cell wall is broken by mechanical stress. For example, for fungal, yeast, bacterial, spore and plant cells, which have stable cell walls, mechanical methods are especially suitable. Compared to other known methods, purely mechanical disruption methods such as, for example, the use of beads (small spheres made of solid material such as glass, steel, etc.) are distinguished by the fact that even cells having a very tough cell wall can be disrupted within a short time, that, furthermore, large amounts of cells can be processed, and that, owing to the disruption, there is no introduction into the sample of additives which might possibly act in an interfering manner in the subsequent isolation, analysis and characterization of the cellular constituents.

Since the disruption process is of decisive importance to all subsequent steps such as, for example, the isolation, purification, amplification, analysis and detection of cellular constituents, it is expedient to use a standard which allows checking and assessment of the completeness of disruption of the cellular material. Advantageously, such a standard should allow not only assessment of the efficiency of the disruption itself, but also allow checking of subsequent steps such as sample preparation, extraction, concentration, isolation, purification, reverse transcription, amplification and/or detection of the cellular constituents obtained from the disrupted cells.

Such a checking concept is, for example, the commercially available ACCURUN® 500 bacterial/fungal sepsis control (BBI Diagnostics, West Bridgewater, Plymouth, USA), which is also described in Clin Chem, Med 2006; 44(4): A8 by Kessler, H. H. et al. This is an external checking concept using a reference sample in which three control organisms, viz. a Gram-positive bacterium (*S. aureus*), a Gram-negative bacterium (*P. aeruginosa*) and a yeast fungus (*C. albicans*), which have previously been inactivated by heat treatment are introduced into negative human plasma. This reference sample is analysed in parallel to the cellular material to be analysed (sample cellular material) using the method which is also used for the sample cellular material. However, a general disadvantage of external controls is that rarely occurring errors, for example pipetting errors, which only affect the sample cellular material cannot be captured by the checking system.

US 2007/0015139 A1 describes a checking concept for the validation of results in nucleic acid assay methods, in which microorganisms are added to the sample to be analysed prior to lysis of the cellular material. This is an internal standard, in that the sample cellular material and the reference cellular material are processed together in one reaction vessel. However, for this checking concept, it is also necessary for the standard to be added to the sample in a separate method step in addition to the reagents, and this likewise represents a potential source of error.

It is an object of the present invention to provide a reagent for disrupting cellular material, containing an internal standard completely integrated into the reagent for the purposes of checking and assessing the completeness of disruption of the cellular material and subsequent steps.

It has now been found that, surprisingly, the beads used to disrupt the cellular material can be coated with reference cells which, during disruption of the sample cellular material using the beads, are disrupted together with the sample cellular material. In this way, an internal standard completely integrated into the reagent for the purposes of checking and assessing the completeness of disruption of the cellular material and subsequent steps is obtained.

Coating of different types of beads, more particularly dextran beads and glass beads, with cells is known in principle and described, for example, by Dietrich, F. and Lelkes, P. I. in Angiogenesis (2006) 9: 111-125; by wÖthler, W. et al. in Exptl Cell Res 74 (1972); by Kalish, D. I. in Biochimica et Biophysica Acta, 506 (1978) 97-119; by Sanford, G. L. et al. in In Vitro Cell Dev. Biol. Animal 38: 493-504, October 2002; and by Klinefelter, G. Y. and Ewing, L. L. in In Vitro Cell Dev. Biology Vol. 24, 6 (6 Jun. 1988).

The present invention therefore provides a reagent for disrupting cellular material (sample cellular material), containing a standard completely integrated into the reagent for the purposes of checking and assessing the completeness of disruption of the cellular material and for the purposes of checking and assessing subsequent steps, comprising at least one step selected from sample preparation, extraction, enrichment, isolation, purification, reverse transcription, amplification and detection of the cellular constituents obtained from the disrupted cells or a combination of a plurality of or all of these steps, comprising beads, on the surface of which reference cells are attached or the surface of which is at least partly coated with reference cells (reference cellular material) as a standard. Additional coating with a protective shell for the additional stabilization of the reference cells applied to the beads, for example with self-assembling polymers, is likewise conceivable.

The reagent can consist of the beads and the reference cells attached thereto, or it can contain further constituents, for example an aqueous or organic liquid, preferably water, a buffer solution, a nutrient solution for the cells or an isotonic aqueous solution, preferably a saline solution, or—also in the dry state—buffer components, salts, nutrients for the cells or the like. A preferred embodiment is one in which the reagent contains, in a known amount, a suspension of cells attached to beads in an aqueous solution or water.

In the context of the invention, the sample cellular material is understood to mean the cellular material to be analysed. Said cellular material can be of plant, animal and/or human origin, have been collected from tissue cultures or cell cultures or originate from bacteria, fungi, microscopic algae and protozoa. The material can have been obtained from living, fossil or mummified samples, soil samples, cultures, concentrates, faeces, sewage sludge, sewage, forensic samples and/or foodstuffs. It can be naturally occurring cellular material as well as genetically modified cellular material.

In the context of the invention, a substance allowing the identification of variations and errors in the processing and analysis of the sample to be analysed is referred to as an internal standard. The internal standard is used as a relative reference value which shows the effect of method parameters on the outcome of a method and thus allows validation of the quality of the method. In contrast to an external standard, an internal standard is present during the entire method in the same vessel as the sample to be analysed and is processed and analysed simultaneously therewith.

In the context of the invention, the standard is referred to as completely integrated into the reagent when it is connected to the reagent in such a way that the user, through sole addition of the reagent, adds both the reagent itself and the standard to the sample and a separate step for the addition of the standard is not necessary, as is the case for the methods known from the prior art. This is achieved in the present invention by the surface of the beads which are used for the mechanical disruption of the sample cellular material being at least partly coated with the reference cells used as a standard.

Since whole cells are used as a standard, the reagent according to the invention allows not only checking and assessment of the actual cell disruption, but also checking and assessment of subsequent steps such as sample preparation, extraction, enrichment, isolation, purification, reverse transcription, amplification and detection of the cellular constituents obtained from the disrupted cells. In the context of the invention, cellular constituents are preferably proteins, ribonucleic acids (RNA) and deoxyribonucleic acids (DNA), particularly preferably DNA.

A multiplicity of cells can be used as reference cells. The cells can be of plant, animal and/or human origin, have been collected from tissue, tissue cultures or cell cultures or originate from bacteria, fungi, microscopic algae and protozoa. They can be naturally occurring cellular material as well as genetically modified cellular material. Preferably, the cells used as a reference are naturally occurring and/or genetically modified microorganisms such as bacteria, archaea, fungi, spores, microalgae and protozoa. In the context of the invention, particular preference is given to using an organism which is not a (human) pathogen under normal circumstances and can therefore be shipped and handled without any special safety precautions (e.g. *E. coli*).

In addition, the standard material is selected such that it is extremely similar in its mechanical properties to the sample material. Which specific reference cellular material is used as an internal standard thus depends on the nature of the sample cellular material. It is also possible to simultaneously use a plurality of cell types for coating the beads, for example in order to be able to use the same broad-purpose reference material preparation together with a plurality of sample materials.

The beads used in the reagent can, for example, consist of glass, metal, ceramic or other porous materials, or tungsten carbide. In a preferred embodiment, the beads are glass beads.

The size of the beads is dependent on the nature and the amount of the cellular material to be lysed. For instance, efficient disruption of animal or plant tissue per unit time generally requires larger beads than the disruption of bacteria or yeast cells. In the context of the invention, the size of the beads is preferably from 0.01 to 10 mm, particularly preferably from 0.05 mm to 2 mm, more preferably from 0.1 to 0.8 mm and in particular from 0.2 to 0.6 mm.

According to the invention, the surface of the beads is coated with reference cells. Applied to the surface of the beads are preferably from $10^2$ to $10^9$ reference cells, particularly preferably from $10^3$ to $10^8$ reference cells and in particular from $10^4$ to $10^7$ reference cells, based on an amount of 100 mg of beads.

Moreover, the surface of the beads which is coated with the reference cells can be provided with an additional protective layer, for example composed of self-assembling polymers, in order to additionally stabilize the reference cells.

To disrupt the cellular material, preferably an amount of from 10 to 1000 mg of coated beads per ml of sample material, particularly preferably an amount of from 20 to 800 mg of beads per ml of sample material and in particular an amount of from 30 to 600 mg of beads per ml of sample material is added to the sample and brought to mechanical disruption. The amount of coated beads which is used in each case per ml of sample material is dependent not only on the quantity of beads but also on the density of the bead material used.

The invention further comprises the use of the reagent according to the invention or of the beads as an internal standard for checking and assessing the completeness of disruption of cellular material and subsequent steps, comprising at least one step selected from sample collection, sample preparation, extraction, enrichment, isolation, purification, reverse transcription, amplification and detection of the cellular constituents obtained from the disrupted cells or a combination of a plurality of or all of these steps. More particularly, the reagent according to the invention is suited to a use of the kind in which the constituents obtained from the disrupted cells are nucleic acids, preferably deoxyribonucleic acids. The nucleic acids obtained from the reference cellular material (reference nucleic acids) can, for example, after cell disruption, be isolated and purified from the sample together with the nucleic acids of the sample cellular material according to methods known to a person skilled in the art, for example using the QIAamp DNA Kit from QIAGEN (Hilden, Germany), and quantified by quantitative real-time PCR (qRT-PCR), in which one or more nucleic acids isolated from the reference cells are used as an internal standard for said steps which follow disruption.

In this case, for the analysis, reference nucleic acids distinguishable from the nucleic acids of the sample, for example on the basis of the sequence, are of course selected.

The method is not restricted in this case to the analysis of one reference nucleic acid sequence. It is of course also possible to use two or more different nucleic acid sequences from the reference cells as an internal standard.

In the use according to the invention, the sample cellular material can be of plant, animal and/or human origin, have been collected from tissue cultures or cell cultures or originate from bacteria, fungi, microscopic algae and protozoa. The material can have been obtained from living, fossil or mummified samples, soil samples, concentrates, cultures, preparations, faeces, sewage sludge, sewage, forensic samples and/or foodstuffs. It can be naturally occurring cellular material as well as genetically modified cellular material. Preferably, the sample cellular material is naturally occurring or genetically modified microorganisms.

The invention further provides a method for preparing reference beads, comprising the following steps:
1. admixing the beads with a suspension containing the reference cells,
2. drying the suspension in the presence of the beads, wherein the reference cells are attached to the beads, coat them or are bonded to them.

Optionally, the method can additionally comprise a third step of further coating the dried cells with a protective layer consisting, for example, of polymers suitable for protecting the dried cells additionally against premature degradation due to long storage under environmental conditions.

The reference cell-containing suspension can be a suspension in water, a buffer, an organic solvent, more particularly alcohol, a saline solution, a culture medium or the like. The concentration of the reference cells in the suspension is dependent on the desired number of reference cells per bead unit of measurement, the preferred range of which has already been specified above, and on the volume of the suspension used to coat the beads. In respect of efficient coating of the beads, the concentration should be selected as high as possible, whereas particularly stringent checking of the subsequent process steps is achieved in particular when the concentration of reference cells is selected as low as possible, preferably in the range just above the detection limit to be expected of the biomolecule to be detected from the reference cell. Preference is given to using a ratio of reference cell suspension to the beads to be coated (µl/mg) of 0.1-10, particularly preferably 0.15-7.5, more preferably 0.2-5 and in particular 0.25-2.5.

Drying of the cell suspension on the beads can be performed by simply incubating the suspension at room temperature (15-30° C.), preferably under sterile conditions, such as in a laminar flow cabinet, by carefully heating the suspension containing the cells and the beads (preferably 30-50° C.), optionally under a slight vacuum or in an inert gas stream, or using a range of further methods known to a person skilled in the art.

The invention further provides a method for disrupting cellular material using a completely integrated internal standard, comprising the following steps:
1. mixing the reagent according to the invention or the beads according to the invention with a sample containing the cellular material to be lysed (sample cellular material),
2. simultaneously disrupting the sample cellular material and the reference cellular material by mechanical action on the mixture.

In this case, mixing of the reagent according to the invention or the beads according to the invention with a sample containing the cellular material to be lysed (sample cellular material) can be performed either by adding the reagent/beads to the sample or by collecting the sample in a vessel already containing the reagent/beads. In particular, when the sample is solid cellular material such as tissue, etc., it is expedient to suspend the sample cells in an appropriate buffer before adding the reagent. In this case, the buffer can contain a range of further agents such as, for example, substances for stabilizing nucleic acids, for deactivating nucleases and/or for lysing proteins (proteinases). More liquid cellular material such as whole blood samples can, too, be diluted by adding water or appropriate buffer solutions prior to mixing with the reagent according to the invention or the beads according to the invention. In particular, it is critical to adjust the sample complexity or the viscosity of the mixture containing the reagent and the sample in the matrix thereof such that the mechanical disruption is efficient. The internal control can in this context be used as a standard for assessing the suitability of the disruption conditions. Added to the sample is preferably an amount of from 10 to 1000 mg of coated beads per ml of sample material, particularly preferably an amount of from 20 to 800 mg per ml of sample material and even more preferably an amount of from 30 to 600 mg of beads per ml of sample material. The amount is then dependent on material and density, and on the size of the beads used.

A person skilled in the art is aware of various methods and instruments for using beads to achieve disruption of cellular material by mechanical action thereon. Here, examples include, for example, ball mills and mixer mills, planetary mills, and the use of ultrasound. In the context of the invention, the cellular material is disrupted preferably with vibrational mixing (so-called vortexing) or by vertical mixing (e.g. using the QIAGEN Tissuelyser), preferably at room temperature or with careful heating. The duration and intensity of the mechanical disruption is dependent on the cell type to be disrupted and on the sample matrix, and this is known to a person skilled in the art. Since the reference cellular material is used as an internal standard for checking the completeness of disruption, it is expedient to use, as reference cellular material, cells which can be disrupted under the same conditions as the sample cellular material or stronger conditions. The duration of the vortexing is preferably from 1 to 20 min, particularly preferably from 3 to 12 min and in particular from 5 to 10 min.

Preferably in the context of the invention, the mixture of reference cellular material and sample cellular material is first disrupted by purely mechanical means in a method step referred to as prelysis and, after subsequent addition of proteinases such as, for example, proteinase K and possibly further chaotrope- and/or detergent-containing lysis buffers, for example Buffer AL or Buffer QSL from QIAGEN (Hilden, Germany), lysed as a result of the combined effect of the mechanical action of the beads and of the enzymatic or chemical effect of the lysis buffer with inactivation or enzymatic degradation of proteins, especially nucleases. The preferred duration of the prelysis, too, is dependent on the sample to be disrupted. Preferably, the prelysis is performed by vortexing the mixture of sample cellular material and reference cellular material for from 1 to 20 min, particularly preferably for from 3 to 12 min and in particular for from 5 to 10 min at the highest setting, using appropriate sample-vessel holders.

The disruption of the cellular material can additionally also be performed using a mixture of the coated beads according to the invention and uncoated beads of the same material or of a different material, and the uncoated beads can be of the same size as or of a different size to the coated beads and can also comprise a mixture of uncoated beads of varying size.

The invention also comprises a kit for detecting nucleic acids in cellular material, containing the reagent according to the invention or the beads according to the invention and optionally appropriate primers for amplifying the sample nucleic acids and/or reference nucleic acids in subsequent PCR methods or other nucleic acid amplification technologies or nucleic acid detection technologies. Particularly suitable for the approach of the invention are, in this case, so-called quantitative real-time PCR methods (qRT-PCR) or qualitative or quantitative isothermal amplification technologies.

Alternatively, the reference reagent can also be used in a sufficiently high concentration so that it can be detected in a subsequent detection reaction without amplification. In the case of such a use of the reference reagent, specifically the process of sample disruption and of sample preparation and of isolation of the target molecule to be detected is checked, whereas the amplification reaction is not checked. This can, for example, be advantageous when particular process steps are to be specifically checked.

In the context of the invention, a primer is understood to mean an oligonucleotide which can hybridize to a nucleic acid sequence (from the reference cellular material or the sample cellular material) to form a double-stranded region. Said double-stranded region can be utilized as a starting point in amplification, for example by qRT-PCR, according to methods known to a person skilled in the art.

By means of the experiments explained in detail in the following examples, it was shown that the beads according to the invention are suitable both for checking the completeness of the disruption of the cellular material and as an internal standard for subsequent analyses of particular cellular constituents such as, for example, qRT-PCR using DNA. Moreover, it was shown that it is possible to prepare reference cell-coated beads, the cells themselves of which are largely still intact after storage for more than one year at room temperature and can thus be used as an internal standard for checking cell disruption and subsequent steps.

DESCRIPTION OF THE FIGURES

FIG. 1 shows the qRT-PCR-determined $C_T$ values for the amplification of *E. coli* DNA, which was disrupted by mechanical action using glass beads.

EXAMPLES

Example 1: Preparation of the Reference Cell-Coated Beads

An *E. coli* culture was cultivated in an LB culture medium (lysogeny broth medium, G. Bertani *J. Bacteriol.*, 1951, 62(3), 293-300). Using a counting chamber, the cell count in said medium was determined under the microscope to be $3.03 \times 10^9$ per ml. The culture was diluted with further LB medium to a concentration of $2 \times 10^7$ cells per ml. 1 ml was taken from this cell suspension, and the cells were pelleted by centrifugation. The pellet obtained was suspended in 1 ml of a 0.9% NaCl solution (aqueous). 50 µl of this suspension were, in each case, added to 100 mg of glass beads (600 µm, Sigma G8772, Lot No. 100 K5339), and the solution was allowed to dry overnight in a laminar flow cabinet. The number of cells was thus $1 \times 10^6$ cells per 100 mg of glass beads.

Example 2: Lysis of Whole Blood

Five batches (each 100 mg) of the coated beads obtained according to example 1 were in each case stored for 1 year at 2-8° C. or 25±3° C. Subsequently, the stored beads were introduced into human whole blood, and the coated bacterial cells were disrupted in this biological matrix by mechanical lysis. This prelysis was followed by QIAGEN sample preparation using the below-described QIAamp DNA Blood Mini Kit (QIAGEN, Hilden, Germany) according to the "QIAamp DNA Mini Kit and QIAamp DNA Blood Mini Kit" handbook (November 2007) in order to isolate and purify the DNA from the disrupted bacterial cells and the human DNA originating from the leukocytes in the blood.

The mechanical disruption procedure referred to as prelysis was optimized in preceding experiments to the effect that optimal disruption of bacterial and fungal cells was achieved in the blood sample material. In blood, optimal disruption was achieved by five-minute vortexing of the sample with the glass beads in a 2:1 mixture of blood and prelysis buffer (containing Tris, EDTA and Triton X-100). The subsequent experiments for analysing the reference beads were therefore carried out using the same prelysis protocol, in order to determine the disruption efficiency of the bacterial cells dried on the beads. For comparative purposes, the analyses were carried out with and without prelysis. The aim of this comparison was, in particular, to show whether prelysis is still necessary when using the coated beads which have already been stored for over a year, or whether possibly, after storage for one year, the cells dried on the beads are no longer intact and the DNA is consequently already free, making prelysis redundant and thus eliminating the checking function of the reference beads. Furthermore, controls were concomitantly carried out which contained, freshly spiked into blood, the same amount of bacteria which were dried on the coated beads.

Cell disruption was carried out with the following samples:
1. three batches of the beads stored at 5° C. (100 mg in each case) and, in each case, 600 µl of freshly thawed blood with prelysis (referred to as WP-5 hereinafter);
2. three batches of the beads stored at 25° C. (100 mg in each case) and, in each case, 600 µl of freshly thawed blood with prelysis (WP-25);
3. two batches of the beads stored at 5° C. (100 mg in each case) and, in each case, 600 µl of freshly thawed blood without prelysis (no prelysis) (NP-5);
4. two batches of the beads stored at 25° C. (100 mg in each case) and, in each case, 600 µl of freshly thawed blood without prelysis (no prelysis) (NP-25);
5. three batches of a control sample composed of 200 mg of uncoated beads and, in each case, 600 µl of blood admixed with $1.07 \times 10^6$ *E. coli* cells with prelysis (C-WP);
6. three batches of a control sample composed of 200 mg of uncoated beads and, in each case, 600 µl of the *E. coli*-spiked blood described in point 5 without prelysis (no prelysis) (C-NP);
7. three control samples each composed of 600 µl of unspiked blood (C-B).

To prepare the *E. coli*-spiked blood samples, 10 ml of blood were admixed with 143 µl of an *E. coli*-glycerol stock culture which contained $1.25 \times 10^8$ cells per ml.

For the disruption of the cells, 600 µl of freshly thawed blood (for samples WP-5, NP-5, WP-25, NP-25, C-B) or 600 µl of *E. coli*-spiked blood (for samples C-NP, C-WP) in 300 µl of SPL1 buffer were added to 200 mg of the untreated beads (C-NP, C-WP, C-B) or 100 mg of the coated beads (WP-5, NP-5, WP-25, NP-25) in a 1.5 ml sample vessel from Eppendorf. Subsequently, the samples with prelysis (WP-5, WP-25, C-WP) were vortexed for five minutes at the highest setting. Alternatively, incubation was carried out for five minutes at room temperature (samples without prelysis). After the glass beads had sunk, 600 µl of the supernatant were transferred to a new sample vessel and, after addition of 60 µl of proteinase K, briefly mixed by vortexing. After addition of 450 µl of Buffer AL from QIAGEN, the sample was vortexed for a further 15 seconds. The above-described steps were carried out in a laminar flow cabinet. The samples were then, in each case, incubated for ten minutes at 56° C. and thereafter briefly centrifuged, admixed with 750 µl of a mixture of 80% ethanol and 20% Buffer AL from QIAGEN (Hilden, Germany) and vortexed for 15 seconds. The entire reaction mixes were, in each case, transferred to Extender Tubes from QIAGEN (Hilden, Germany) which were fitted onto QIAamp Mini Columns from QIAGEN (Hilden, Germany). The lysate was then drawn under vacuum through the QIAamp Mini Columns, with the released nucleic acid binding to the silica matrix of the column. Subsequently, the column was washed twice with, in each case, 700 µl of Buffer AW1 from QIAGEN (Hilden, Germany). The wash solution was removed under reduced pressure. Thereafter, the column was washed twice with, in each case, 750 µl of Buffer AW2 from QIAGEN (Hilden, Germany), and the wash solution was removed under reduced pressure. Subsequently, the QIAamp Mini Column was removed from the vacuum device, transferred to a new sample vessel and dried by three-minute centrifugation at 15 000 g. The column was transferred to a new vessel and dried in a heating block for an additional five minutes at 56° C. The DNA was subsequently eluted with 100 µl of ultrapure water, with incubation at room temperature for one minute on the membrane of the spin column before the eluate was obtained by centrifugation at 15 000 g for 1 minute. The eluates obtained were analysed photometrically in order to determine the total DNA yield, i.e. the human DNA, including *E. coli* DNA, obtained from the blood, with the proportion of the DNA obtained from the reference cellular material with respect to the DNA obtained from the sample being low. The results are shown in table 1. In addition, qRT-PCR analysis was carried out for the quantitative specific detection of the *E. coli* DNA.

TABLE 1

| | | | | Yield µg/elution | | | |
|---|---|---|---|---|---|---|---|
| Sample | Batch | A260 | A260/A280 | [µg] | Mean | SD[1] | CV[2] % |
| Coated beads with prelysis, stored at 5° C. (WP-5) | 1 | 0.30 | 1.95 | 8.49 | 7.7 | 0.8 | 9.9 |
| | 2 | 0.27 | 1.93 | 7.80 | | | |
| | 3 | 0.24 | 1.93 | 6.66 | | | |
| Coated beads with prelysis, stored at 25° C. (WP-25) | 1 | 0.26 | 1.92 | 7.26 | 7.5 | 1.2 | 15.9 |
| | 2 | 0.33 | 1.94 | 9.03 | | | |
| | 3 | 0.23 | 1.90 | 6.15 | | | |
| Coated beads without prelysis, stored at 5° C. (NP-5) | 1 | 0.23 | 1.95 | 6.78 | 5.9 | 0.9 | 15.0 |
| | 2 | 0.17 | 1.88 | 5.01 | | | |
| Coated beads without prelysis, stored at 25° C. (NP-25) | 1 | 0.19 | 1.91 | 5.40 | 5.6 | 0.2 | 4.3 |
| | 2 | 0.21 | 1.88 | 5.88 | | | |
| Control *E. coli* with prelysis (C-WP) | 1 | 0.18 | 2.68 | 3.78 | 4.3 | 0.5 | 11.8 |
| | 2 | 0.17 | 1.93 | 4.98 | | | |
| | 3 | 0.14 | 1.93 | 4.11 | | | |
| Control *E. coli* without prelysis (C-NP) | 1 | 0.20 | 1.91 | 5.85 | 5.6 | 0.2 | 4.1 |
| | 2 | 0.20 | 1.92 | 5.70 | | | |
| | 3 | 0.18 | 1.82 | 5.31 | | | |

TABLE 1-continued

| | | | | Yield µg/elution | | | |
|---|---|---|---|---|---|---|---|
| Sample | Batch | A260 | A260/A280 | [µg] | Mean | SD[1] | CV[2] % |
| Control blood (C-B) | 1 | 0.20 | 1.90 | 5.58 | 4.9 | 0.7 | 14.5 |
| | 2 | 0.17 | 1.88 | 5.07 | | | |
| | 3 | 0.13 | 1.86 | 3.90 | | | |

[1]SD: standard deviation;
[2]CV: coefficient of variation

The amount of total DNA was determined by photometric measurements of light absorption at a wavelength of 260 nm. It can be clearly seen that the use of the coated beads and also the prelysis procedure, i.e. the vortexing of the sample mixed with the beads, do not have an adverse effect on the total yield of DNA.

The purity of the DNA obtained was determined by means of photometric measurement of the ratio of light absorption at 260 nm to that at 280 nm (A260/A280). The A260/A280 ratio was within the range of between 1.8 and 2.0 for all samples which were disrupted using the coated beads. Consequently, storage of the coated samples for more than one year has no effect on the purity of the DNA obtained.

Example 3: qRT-PCR Analysis for the Specific Detection of *E. coli* DNA

To demonstrate that the *E. coli* DNA from the coated beads is still intact and detectable even after storage for one year, a real-time polymerase chain reaction (qRT-PCR) was carried out for the detection of the *E. coli* DNA in samples WP-5, NP-5, WP-25, NP-25, C-WP and C-NP, which are described in example 2. The reactions were carried out using the FRET probe 5' [6~FAM]CACTACGGTGCTGAAGC-GACAA A[BHQ1a~6FAM] (SEQ ID NO: 1) and the primers 5'CCAGGCAAATCCGGAAAAC3' (SEQ ID NO: 2) and 5'GTACGATTTGATGTTACCTGAT3' (SEQ ID NO: 3) on an ABI Taqman 7900 (Applied Biosystems Inc., Foster City, Calif., USA) in reaction volumes of, in each case, 25 µl (10 µl of template, 0.6 µl of a 10 µM solution of the FAM-BHQ-functionalized FRET probe, 12.5 µl of QIAGEN 2× QuantiTect Multiplex PCR, 0.6 µl of a mixture of the two primers, each as a 10 µM solution, and 1.3 µl of ultrapure water). A total of 40 cycles was carried out, with each cycle comprising the following steps: denaturation (15 min at 95° C.), annealing (45 s at 94° C.) and elongation (75 s at 60° C.).

The $C_T$ (threshold cycle) values thus determined are shown in table 2.

TABLE 2

| | $C_T$ values | | | |
|---|---|---|---|---|
| Sample | $C_T$ | Mean | SD[1] | CV[2] [%] |
| Coated beads with prelysis, stored at 5° C. (WP-5) | 19.49 | 19.31 | 0.20 | 1.04 |
| | 19.35 | | | |
| | 19.09 | | | |
| Coated beads with prelysis, stored at 25° C. (WP-25) | 20.85 | 20.67 | 0.20 | 0.95 |
| | 20.46 | | | |
| | 20.70 | | | |
| Coated beads without prelysis, stored at 5° C. (NP-5) | 20.87 | 20.36 | 0.72 | 3.54 |
| | 19.85 | | | |
| Coated beads without prelysis, stored at 25° C. (NP-25) | 22.85 | 22.75 | 0.14 | 0.60 |
| | 22.65 | | | |

TABLE 2-continued

| Sample | $C_T$ | Mean | SD[1] | CV[2] [%] |
|---|---|---|---|---|
| Control E. coli with prelysis (C-WP) | 21.65<br>22.29<br>22.29 | 22.08 | 0.37 | 1.67 |
| Control E. coli without prelysis (C-NP) | 24.99<br>24.64<br>25.43 | 25.02 | 0.40 | 1.58 |

[1]SD: standard deviation;
[2]CV: coefficient of variation

Although a direct comparison between the samples which were treated with the coated beads and those which were spiked with E. coli cells is difficult owing to the different starting cultures of E. coli bacteria, it can nevertheless be clearly seen that the E. coli DNA on the coated beads was still very highly amplifiable and detectable by qRT-PCR even after storage for one year. Furthermore, it can be seen that the prelysis has a significantly positive effect on the $C_T$ value determined in subsequent amplification, indicating that the majority of the cells was still intact and required disruption. This is also illustrated in FIG. 1, which shows the qRT-PCR-determined $C_T$ values according to disruption method. The $C_T$ values of those blood samples which were disrupted using the coated beads (WP-5, WP-25 and NP-5, NP-25) are below the $C_T$ value which was determined for the DNA obtained from just the blood sample (C-WP and C-NP), and this was the case for both the beads stored at 5° C. and the beads stored at 25° C. In this connection, a comparison should be made between the two sets of samples treated according to the same method, i.e. those with prelysis (WP) and those without prelysis (NP). A comparison of the samples which were subjected to prelysis with those which were disrupted without prelysis further shows that the use of the prelysis step has a significantly positive effect on the $C_T$ value obtained when the coated beads are used for the cell disruption, indicating that the majority of the E. coli cells in the coating was still intact and allowed disruption even after storage for more than one year.

This applied to both the coated beads stored at 25° C. and those stored at 5° C. In summary, examples 2 and 3 show that the cells applied to glass beads are stable over a long period (t>1 year) and can, even after storage for one year, be used for checking the completeness of disruption and for assessing subsequent analyses such as, for example, qRT-PCR.

The invention claimed is:

1. A reagent for disrupting a sample cellular material, comprising:
   beads, the surface of which is at least partly coated with reference cells, wherein the reference cells are capable of being an internal standard completely integrated into the reagent for checking and assessing the completeness of disruption of a sample cellular material and subsequent steps selected from sample preparation, extraction, enrichment, isolation, purification, reverse transcription, amplification and detection of the cellular constituents obtained from the disrupted cells, and a combination of a plurality of or all of these steps,
   wherein: the beads consist of glass, metal, ceramic or other porous materials or tungsten carbide; the size of the beads is from 0.05 mm to 2 mm; and the beads have been created by drying out a suspension comprising the reference cells in the presence of the beads, thereby attaching the reference cells to the beads, coating the beads with the reference cells, or bonding the reference cells to the beads.

2. The reagent of claim 1, wherein the reference cells are naturally occurring microorganisms.

3. The reagent of claim 1, wherein the reference cells are genetically modified microorganisms.

4. The reagent of claim 1, wherein the beads are glass beads.

5. Beads, the surface of which is at least partly coated with dried-up reference cells, wherein: the beads consist of glass, metal, ceramic or other porous materials or tungsten carbide; the size of the beads is from 0.05 mm to 2 mm; and the beads have been created by drying out a suspension comprising the reference cells in the presence of the beads, thereby attaching the reference cells to the beads, coating the beads with the reference cells, or bonding the reference cells to the beads.

6. The beads of claim 5, wherein the size of the beads is from 0.1 to 0.8 mm or from 0.2 to 0.6 mm.

7. The beads of claim 5, wherein from $10^2$ to $10^9$ reference cells, from $10^3$ to $10^8$ reference cells, or from $10^4$ to $10^7$ reference cells are applied to the surface of 100 mg of beads.

8. The beads of claim 5, wherein the surface of the beads including the reference cells is further coated with an additional protective layer.

9. A method for preparing the beads of claim 5, comprising:
   (a) admixing beads with a suspension containing reference cells in an aqueous solution, wherein the beads consist of glass, metal, ceramic or other porous materials or tungsten carbide and the size of the beads is from 0.05 mm to 2 mm,
   (b) drying the aqueous solution on the beads, and
   (c) optionally coating the beads obtained from step (b) with a protective layer.

10. A method for disrupting a sample cellular material using a completely integrated internal standard, comprising:
    (A) mixing
       (a) the reagent according to claim 1, or
       (b) beads, the surface of which is at least partly coated with dried-up reference cells, wherein the beads consist of glass, metal, ceramic or other porous materials or tungsten carbide, the size of the beads is from 0.05 mm to 2 mm, and the beads have been created by drying out a suspension comprising the reference cells in the presence of the beads, thereby attaching the reference cells to the beads, coating the beads with the reference cells, or bonding the reference cells to the beads,
    with a sample cellular material to be disrupted, and
    (B) simultaneously disrupting the sample cellular material and the reference cells by mechanical action on the mixture of step (A).

11. The method of claim 10, wherein step (B) is performed with vortexing.

12. The method of claim 10, wherein step (B) comprises simultaneously disrupting the sample cellular material and the reference cells using a mixture of:
    (i) the beads the surface of which is at least partly coated with the reference cells, wherein: the beads consist of glass, metal, ceramic or other porous materials or tungsten carbide; the size of the beads is from 0.05 mm to 2 mm; and the beads have been created by drying out a suspension comprising the reference cells in the presence of the beads, thereby attaching the reference cells to the beads, coating the beads with the reference cells, or bonding the reference cells to the beads and
    (ii) beads the surface of which is not coated with the reference cells.

13. The method of claim 10, further comprising performing one or more additional steps selected from sample preparation, extraction, enrichment, isolation, purification, reverse transcription, amplification of the cellular constituents obtained from the disrupted cells, and detection of the cellular constituents obtained from the disrupted cells, wherein the reference cells are used as an internal standard for the one of more additional steps.

14. The method of claim 13, wherein the constituents obtained from the disrupted cells are nucleic acids.

15. The method of claim 14, wherein the nucleic acids are deoxyribonucleic acids.

16. The method of claim 13, wherein the sample cellular material is naturally occurring microorganisms.

17. The method of claim 13, wherein the sample cellular material is genetically modified microorganisms.

18. A kit for detecting nucleic acids in cellular material, containing:
    (i) a reagent of claim 1, or
       beads, the surface of which is at least partly coated with dried-up reference cells, wherein: the beads consist of glass, metal, ceramic or other porous materials or tungsten carbide; the size of the beads is from 0.05 mm to 2 mm; and the beads have been created by drying out a suspension comprising the reference cells in the presence of the beads, thereby attaching the reference cells to the beads, coating the beads with the reference cells, or bonding the reference cells to the beads; and
    (ii) primers for amplifying the nucleic acids from the sample cellular material or from the reference cells.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Synthetic DNA

<400> SEQUENCE: 1
cactacggtg ctgaagcgac aaa                                          23

<210> SEQ ID NO 2
<211> LENGTH: 19
<212> TYPE: DNA
<213> ORGANISM: Artificial Sequence
<220> FEATURE:
<223> OTHER INFORMATION: Synthetic DNA

<400> SEQUENCE: 2
ccaggcaaat ccggaaaac                                               19

<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3
gtacgatttg atgttacctg at                                           22
```